United States Patent [19]

Kaldany

[11] Patent Number: 5,562,613
[45] Date of Patent: Oct. 8, 1996

[54] SUBCUTANEOUS DRUG DELIVERY DEVICE

[75] Inventor: Antoine Kaldany, Chestnut Hill, Mass.

[73] Assignee: InterMED, Inc., Chestnut Hill, Mass.

[21] Appl. No.: 271,148

[22] Filed: Jul. 6, 1994

Related U.S. Application Data

[63] Continuation-in-part of Ser. No. 965,638, Oct. 23, 1992, Pat. No. 5,358,474, which is a continuation-in-part of Ser. No. 908,353, Jul. 6, 1992, abandoned, which is a continuation-in-part of Ser. No. 724,706, Jul. 2, 1991, Pat. No. 5,127,419.

[51] Int. Cl.$^6$ .................................................. A61M 31/00
[52] U.S. Cl. ........................... 604/57; 606/170; 128/754
[58] Field of Search ..................... 604/93, 95, 117, 604/158, 159, 160, 164, 165, 166, 170, 48, 57, 59, 60; 128/749, 751, 753, 754, 755; 606/7, 167, 170, 184, 185, 187

[56] References Cited

U.S. PATENT DOCUMENTS

| | | |
|---|---|---|
| 387,480 | 8/1888 | Alleman . |
| 737,293 | 8/1903 | Summerfeldt . |
| 806,746 | 12/1905 | Miller . |
| 2,634,726 | 4/1953 | Hanson . |
| 2,705,949 | 4/1955 | Silverman ..................... 604/117 X |
| 3,477,423 | 11/1969 | Griffith . |
| 3,606,878 | 9/1971 | Kellogg . |
| 3,662,754 | 5/1972 | Halloran . |
| 3,995,619 | 12/1976 | Glatzer ......................... 128/754 X |
| 4,178,810 | 12/1979 | Takahashi . |
| 4,402,308 | 9/1983 | Scott . |
| 4,411,657 | 10/1983 | Galindo . |
| 4,461,280 | 7/1984 | Baumgartner .................. 604/93 X |
| 4,537,593 | 8/1985 | Alchas .......................... 604/411 |
| 4,578,059 | 3/1986 | Fabricant et al. ............... 604/43 |
| 4,600,014 | 7/1986 | Beraha ........................ 128/754 |
| 4,609,370 | 9/1986 | Morrison ...................... 604/165 |
| 4,699,154 | 10/1987 | Lindgren ...................... 128/754 |
| 4,700,692 | 10/1987 | Baumgartner . |
| 4,701,164 | 10/1987 | Cassou et al. ................. 604/218 |
| 4,702,261 | 10/1987 | Cornell et al. ................ 128/754 |
| 4,735,611 | 4/1988 | Anderson et al. .............. 604/130 |
| 4,776,346 | 10/1988 | Beraha et al. ................ 128/754 |
| 4,820,267 | 4/1989 | Harman ........................ 604/60 |
| 4,842,585 | 6/1989 | Witt .......................... 604/158 |
| 4,871,094 | 10/1989 | Gall et al. ................... 222/386 |
| 4,881,551 | 11/1989 | Taylor ........................ 128/754 |
| 4,900,304 | 2/1990 | Fujioka et al. ................ 604/60 |
| 4,907,598 | 3/1990 | Bauer ......................... 128/753 |
| 4,913,142 | 4/1990 | Kittrell et al. ............... 606/7 |
| 4,917,100 | 4/1990 | Nottke ........................ 128/749 |
| 4,940,061 | 7/1990 | Terwilliger et al. ............ 128/754 |
| 4,958,625 | 9/1990 | Bates et al. .................. 128/754 |
| 4,986,814 | 1/1991 | Burney et al. ................. 604/164 |
| 5,226,426 | 7/1993 | Yoon .......................... 128/753 |
| 5,271,744 | 12/1993 | Kramer et al. ................. 604/51 |
| 5,304,119 | 4/1994 | Balaban et al. ................ 604/51 |
| 5,364,365 | 11/1994 | Wortrich ...................... 604/158 |
| 5,394,887 | 3/1995 | Haaga ......................... 128/754 |
| 5,405,324 | 4/1995 | Wiegerinck ................... 604/60 |
| 5,458,112 | 10/1995 | Weaver ........................ 128/753 |

FOREIGN PATENT DOCUMENTS

| | | |
|---|---|---|
| 0207726 | 7/1987 | European Pat. Off. . |
| 89/10091 | 11/1989 | WIPO . |
| 91/10399 | 7/1991 | WIPO . |

*Primary Examiner*—Randall L. Green
*Assistant Examiner*—V. Alexander
*Attorney, Agent, or Firm*—Hamilton, Brook, Smith & Reynolds, P.C.

[57] ABSTRACT

A subcutaneous drug delivery device having a driving member for advancing a piston, concentrically enclosed by a cannula, to deliver a drug pellet to a subcutaneous tissue site. The piston has a recessed distal platform upon which the pellet rests for delivery when the distal end of the piston is exposed beyond the cannula.

22 Claims, 5 Drawing Sheets

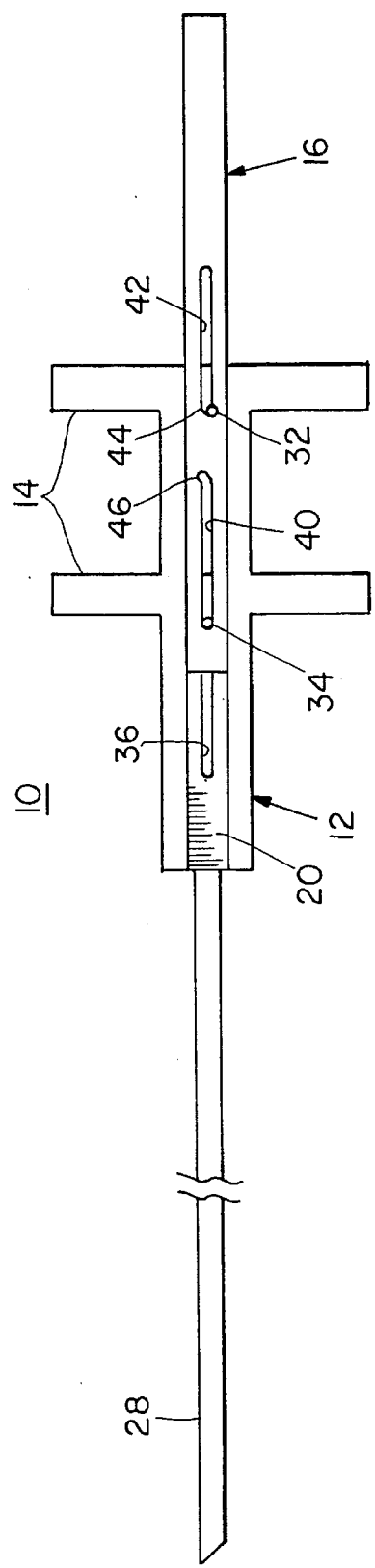
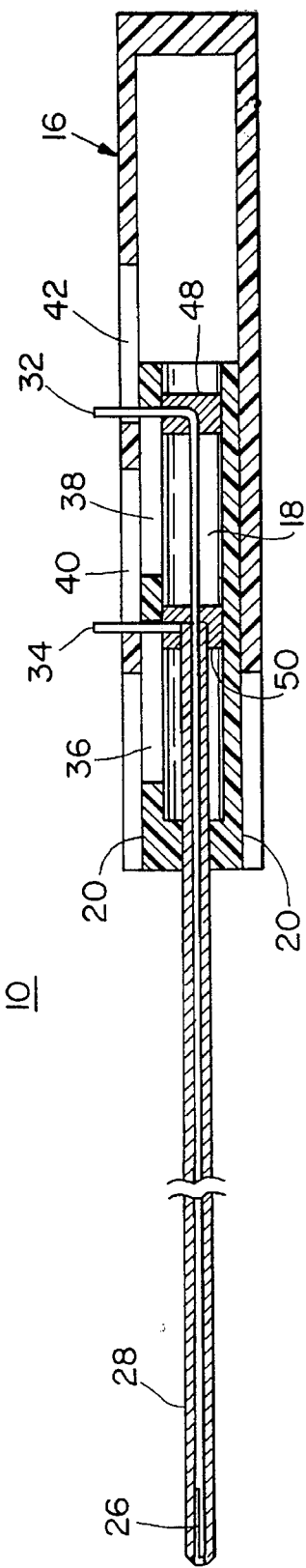

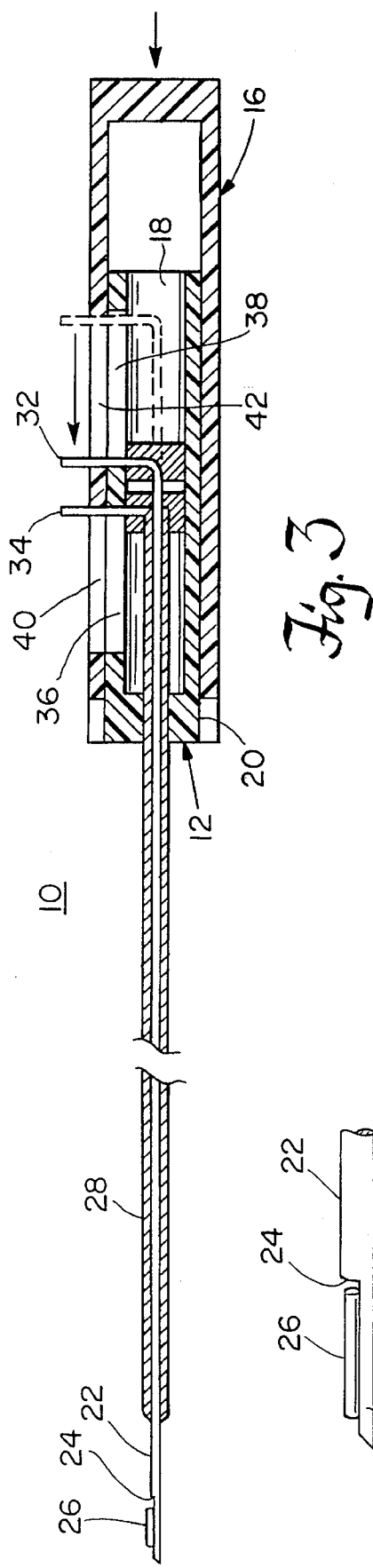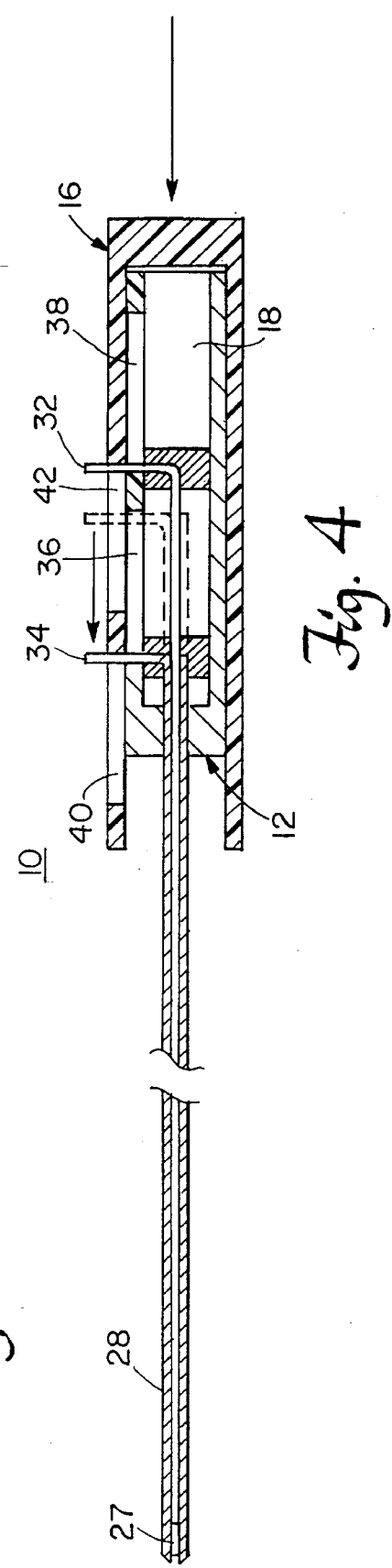

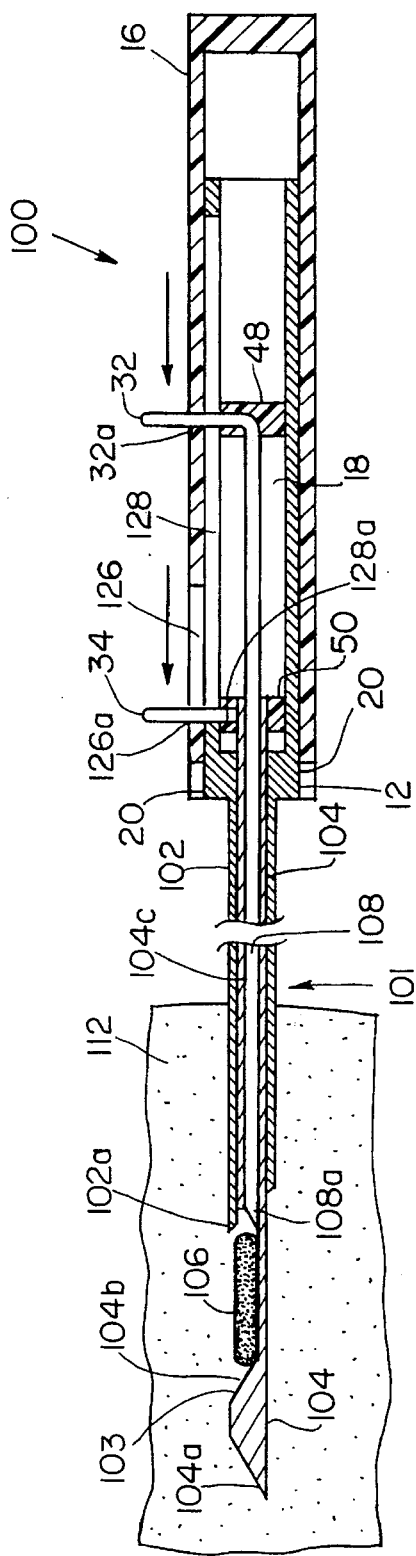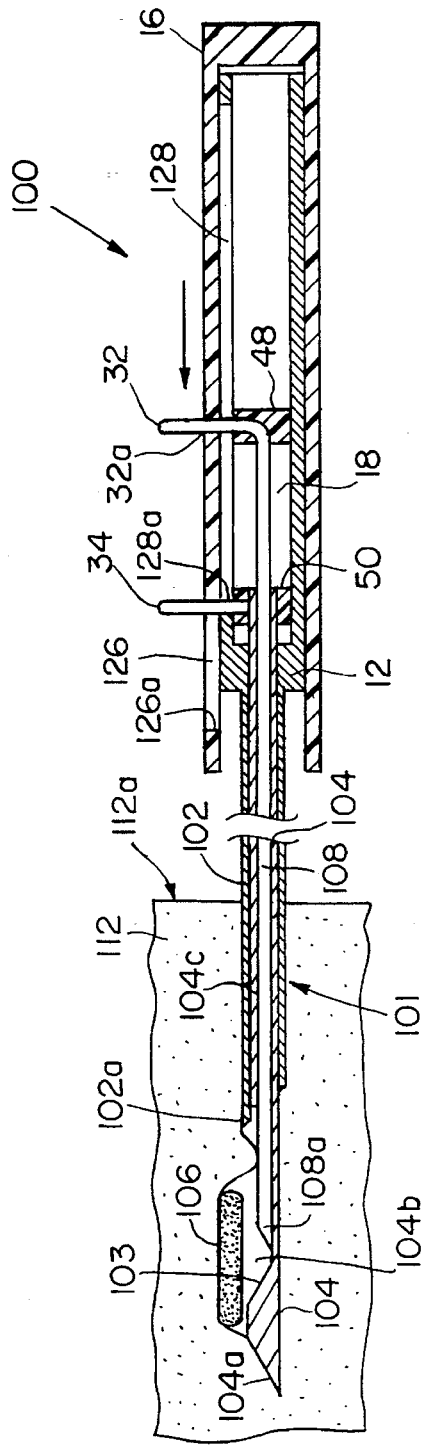

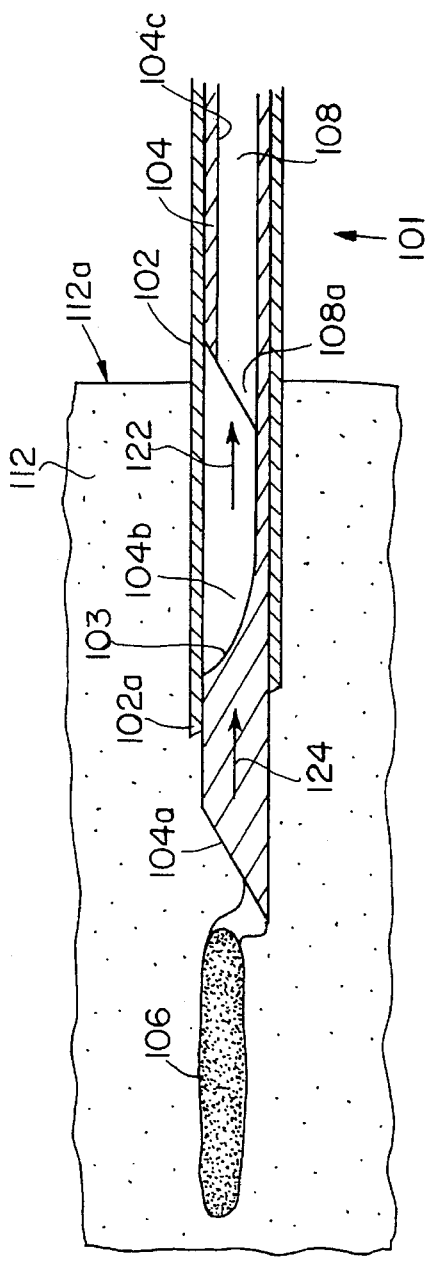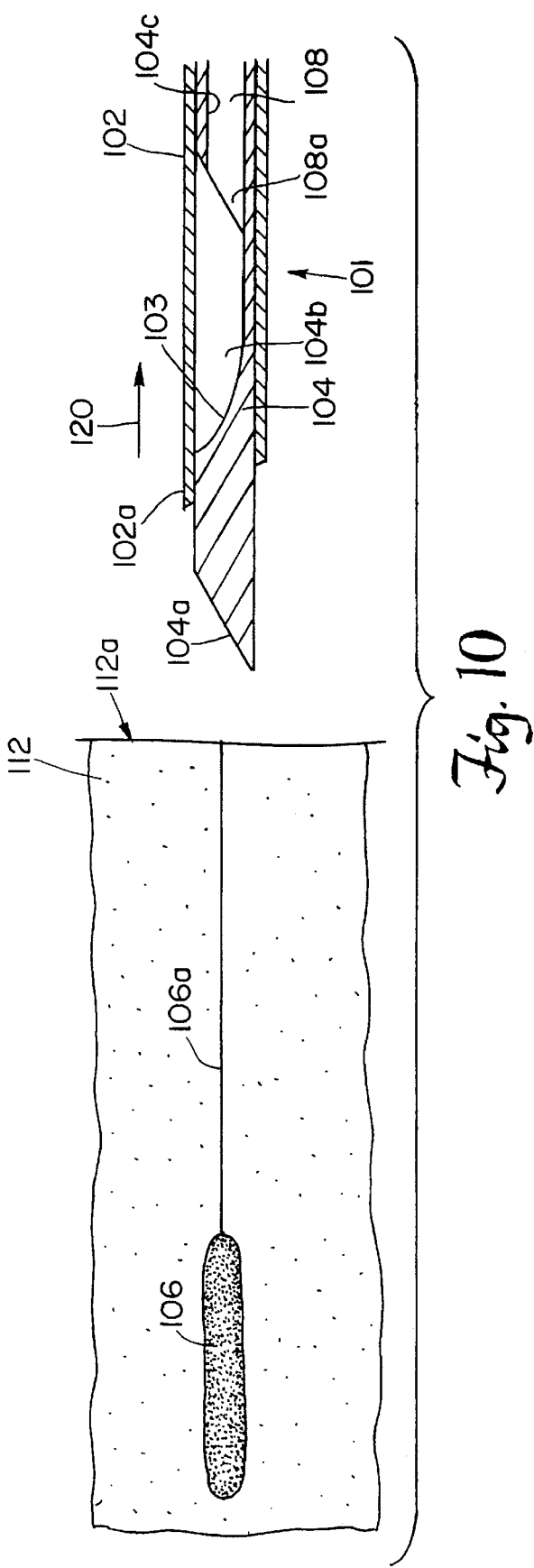

SUBCUTANEOUS DRUG DELIVERY DEVICE

This application is a continuation-in-part of U.S. application 07/965,638 filed on Oct. 23, 1992, now U.S. Pat. No. 5,358,474, which is a continuation-in-part of U.S. application 07/908,353 filed on Jul. 6, 1992, now abandoned, which is a continuation-in-part of U.S. application 07/724,706, filed Jul. 2, 1991, now U.S. Pat. No. 5,127,419 which issued on Jul. 7, 1992, each of which is incorporated herein by reference.

BACKGROUND OF THE INVENTION

Much effort has been expended in recent years to find an effective and superior way of administering drugs to patients' bodies. Products such as the transdermal patch and once-a-day orally administered pills that more precisely deliver drugs have been developed. Such products are a boon to patients for they boost the effectiveness of the drugs and limit side effects by precisely controlling how quickly drugs are released in the body; by keeping drugs at a constant level and by delivering them exactly where needed.

One such development is the injection or implantation of drugs in the form of in microscopic particles or pellets at a disease site. The drugs are encapsulated in polymers or fatty compounds, such as liposomes which permit slow release of the encapsulated drug over time thereby potentially lowering the drugs toxicity.

SUMMARY OF THE INVENTION

The subject invention relates to an improved instrument for subcutaneous delivery of drug pellets to patients. The instrument is comprised of a driving member which sequentially advances a piston having a piston notch at a distal end for supporting the drug to be delivered and a cannula concentrically enclosing the piston during delivery. Note: For reference purposes, the end of the device nearest the driving member is referred to as the proximal end and the end of the device having the piston notch is referred to as the distal end.

The instrument includes a housing with a bore extending along a longitudinal axis of the housing. A track in the housing extends parallel to the bore. The track has a proximal and distal housing slot extending along the longitudinal axis. A piston and a cannula are mounted in the bore and extend coaxially along the longitudinal axis. The driving member is slideably engaged in the track for longitudinal movement therein and the driving member also contains a proximal and distal elongate slot. A piston coupling means extends to the piston through the proximal elongate slot in the housing and the driving member. Optionally, a cannula coupling means extends to the cannula through the proximal elongate slot in the housing and the driving member.

The drug, preferably in slow-release pellet form is placed on the notch when the instrument is in the fully retracted position and the cannula forms a sheath over the pellet. The physician places the distal end of the instrument adjacent the tissue region where the drug is to be delivered and inserts the instrument subcutaneously to the intended delivery spot. Then the driving member is moved distally along the track toward the piston notch. This extends the piston notch beyond the sheath provided by the cannula whereupon the pellet is exposed and can then be deposited at the desired spot. Optionally, as the driving member is moved further along the track the cannula is extended until the cannula coupling means reaches the distal end of the distal housing slot. In this, the fully advanced position, the cannula again covers the piston notch at the tip of the piston and the instrument may be retracted leaving the pellet deposited in the desired tissue site.

In another preferred embodiment, the present invention provides an instrument including a housing having a bore extending along a longitudinal axis of the housing. A track extends parallel to the bore. The track has an elongate housing slot extending along the longitudinal axis. The instrument includes a piston having a distal end. A cannula is mounted concentric with the piston within the bore and extends along the longitudinal axis with a distal end of the cannula extending beyond the distal end of the piston. The cannula has a cannula notch at the cannula distal end for supporting a drug. The cannula notch has a distal surface.

A driving member is slideably engaged in the track for longitudinal movement. The driving member has a hole formed therein. A piston drive pin engages the driving member hole for advancing the piston. The piston drive pin extends from the piston in a direction perpendicular to the longitudinal axis through the housing slot and the driving member hole. As the driving member is moved distally along the track toward the piston distal end, the hole in the driving member is engaged by the piston drive pin and the piston is extended until the distal end of the piston reaches the distal surface of the cannula notch whereupon the piston pushes the drug against the distal surface of the cannula notch to eject the drug laterally from the cannula notch.

In preferred embodiments, an outer tube which is secured to the housing is mounted concentric about the cannula. The outer tube extends along the longitudinal axis and is capable of enclosing the cannula notch. The driving member has an elongate driving member slot which extends along the longitudinal axis and has a notch formed therein. A cannula drive pin engages the notch in the driving member slot for advancing the cannula. The cannula drive pin extends through the housing slot and the driving member slot. As the driving member is moved distally along the track toward the piston distal end, the notch in the driving member slot is engaged by the cannula drive pin and the cannula is extended in unison with the piston until the cannula notch is extended beyond the outer tube. The piston is then further extended to push the drug against the distal surface of the cannula notch to eject the drug.

A significant advantage of the invention is that the physician may advance the piston by unidirectional single-handed movement of the driving member in a single, smooth and uninterrupted motion and precisely deposit the drug at the predetermined tissue site.

BRIEF DESCRIPTION OF THE FIGURES

FIG. 1 is a top view of an embodiment the instrument of this invention.

FIG. 2 is a cross-section side view of the instrument of this invention in the fully retracted position.

FIG. 3 is a cross-section side view of the instrument of this invention in a partially advanced position.

FIG. 3a is an enlarged view of an embodiment of the distal or tip end of the piston.

FIG. 4 is a cross-section side view of the instrument in a fully advanced position.

FIG. 7 is a cross-sectional side view of the instrument of FIG. 5 in a partially advanced position within the tissue.

FIG. 8 is a cross-sectional side view of the instrument of FIG. 5 in a fully advanced position within the tissue to deposit a drug pellet.

FIG. 9 is a cross-sectional side view of the tip of the instrument of FIG. 5 being retracted from the tissue leaving the drug pellet behind.

FIG. 10 is a cross-sectional side view of the portion of tissue containing the deposited drug pellet after the tip of the instrument has been removed.

DESCRIPTION OF A PREFERRED EMBODIMENT

Figure 5:
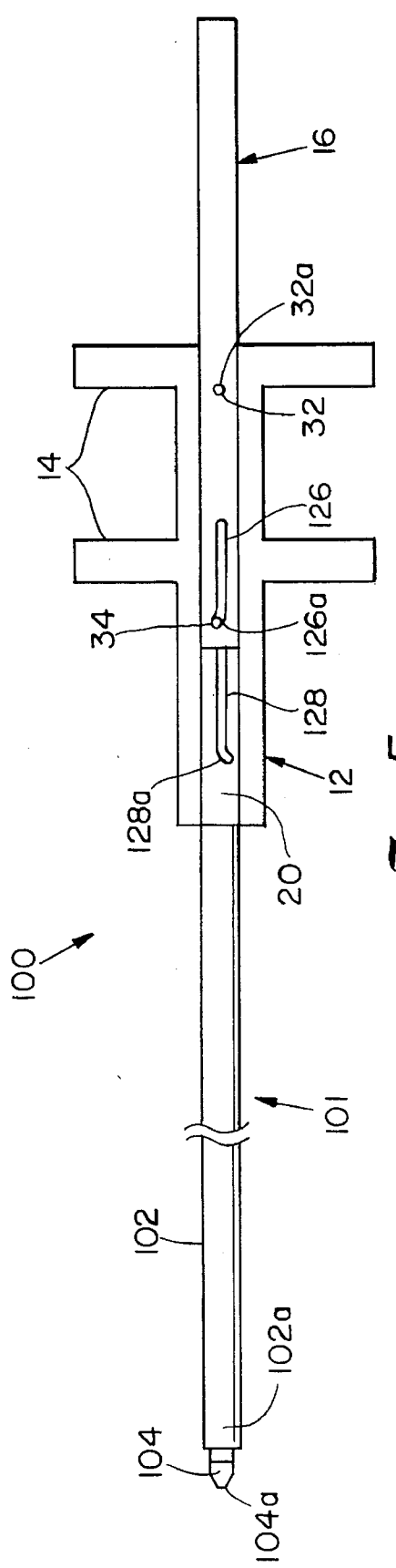
FIG. 5 is a top view of another preferred embodiment of the present invention.

Considering now the drawings in detail, FIG. 1 shows a top view of an embodiment of the instrument. The instrument 10 has a housing 12 with a pair of finger grips 14 extending transverse the longitudinal axis of the housing. A driving member 16 is slideably engaged with a track 20 formed along the longitudinal length of housing 12.

Referring to FIG. 2, which is a cross-sectional side view of the FIG. 1 embodiment, the housing track 20 has an elongate proximal housing slot 38 and an optional elongate distal housing slot 36 which extend along the longitudinal axis. The driving member 16 also has an elongate proximal slot 42 and an optional elongate distal slot 40. The proximal and distal driving member slots 42 and 40, respectively, are provided with notches 42 and 46 respectively at their distal and proximal ends, respectively. The notch in the proximal driving member slot 42 is designated notch 44 and the notch in the distal driving member slot 40 is designated notch 46 (shown most clearly in FIG. 1).

The housing has a cylindrical bore 18 formed therein which extends along the longitudinal axis of the housing 12. Mounted within the cylindrical bore 18 and extending along the longitudinal axis is a piston 22 and a cannula 28 mounted coaxial to the piston 22. The piston 22 and cannula 28 are secured at their respective proximal ends by a piston grip 48, and a cannula grip 50. The piston grip 48 and cannula grip 50 are disc-shaped with a diameter which approximates the diameter of the cylindrical bore. The piston grip 48 and the cannula grip 50 are slideably engaged within the housing bore 18. The piston grip 48 and cannula grip 50 have respective channels formed therein through which drive pins 32 and 34 respectively extend for engagement with the proximal ends of the piston and cannula respectively.

The piston and cannula are preferably formed of rigid sterilizable material such as stainless steel. Other components of the device, including the housing, driving member, piston and cannula grips, etc. are preferably manufactured from low cost plastic material. The use of molded plastic components for the manufacture of the instrument is preferred to lower the cost so that the device can be disposed of after use.

To use the instrument of this invention to subcutaneously deposit a drug, the physician begins with the device in the fully retracted position as shown in FIG. 2 so that the distal end of the cannula encloses the piston. In this position, the driving member 16 is withdrawn to its most proximal position and the cannula drive pin 34 is located at the proximal terminus of housing slot 36 and the distal terminus of driving member slot 40. The piston drive pin is located at the proximal terminus of housing slot 38 and engaged in the notch 44 at the distal terminus of driving member slot 42. Preferably, the drug pellet 26 has been disposed upon the platform provided on piston 28 by the piston notch 24 formed at the distal end of the piston as most clearly shown in FIG. 3A.

With the cannula concentrically enclosing the piston tip and drug pellet 26 the end of the device is positioned at a point within the body proximate to the tissue site for drug delivery. The physician then advances the driving member 16 toward the distal end of the device. As the driving member is advanced, the piston drive pin 32 remains locked in notch 44 resulting in the advance of the distal tip 24 of the piston 22 into the tissue. The cannula drive pin 34, on the other hand, remains stationary. As the driving member 16 advances from the original fully retracted position, the proximal terminus of driving member slot 40 advances toward stationary cannula pin 34.

FIG. 3 shows the relationship of the parts at the point at which the piston 22 is fully advanced and the cannula 28 is fully retracted. In this position, the pellet 26 is now exposed and can be deposited into the tissue and the device withdrawn. The cannula drive pin 34 is now in contact with the proximal termini of both driving member slot 40, and housing slot 36. The piston drive pin 32 is in contact with the distal terminus of housing slot 38, and engages notch 44 at the distal terminus of driving member slot 42. The device may then be withdrawn from the body.

Alternatively, after the pellet is deposited the physician can continue to advance the driving member distally, the resistance of the housing on piston drive pin 32 (which has reached the distal terminus of housing slot 38) forces the piston drive pin out of notch 44 and into driving member slot 42. This results in loss of motion of the piston 22 and the proximal terminus of driving member slot 42 advances toward the piston drive pin 32 as the physician continues to advance the driving member 16. At approximately the same time that the piston drive pin 32 is forced from notch 44, the cannula drive pin 34 begins its distal advance. The cannula drive pin 34 is engaged with notch 46 at the proximal terminus of driving member slot 40. As the driving member 16 is advanced, the cannula drive pin 34 and the cannula 28 itself are driven distally. The cannula in this position, as shown in FIG. 4, encloses the platform 27 formed at the notched end of piston 22 and the device may then be withdrawn from the body.

For deeper penetration into the body, the shaft of the piston and cannula may be elongate and made from a semi-rigid material so that bends can be introduced during insertion, for example, to avoid possible contact with vital organs. The mechanism of sequential piston and cannula advancement is identical in the remote embodiment to that described above.

Figure 6:
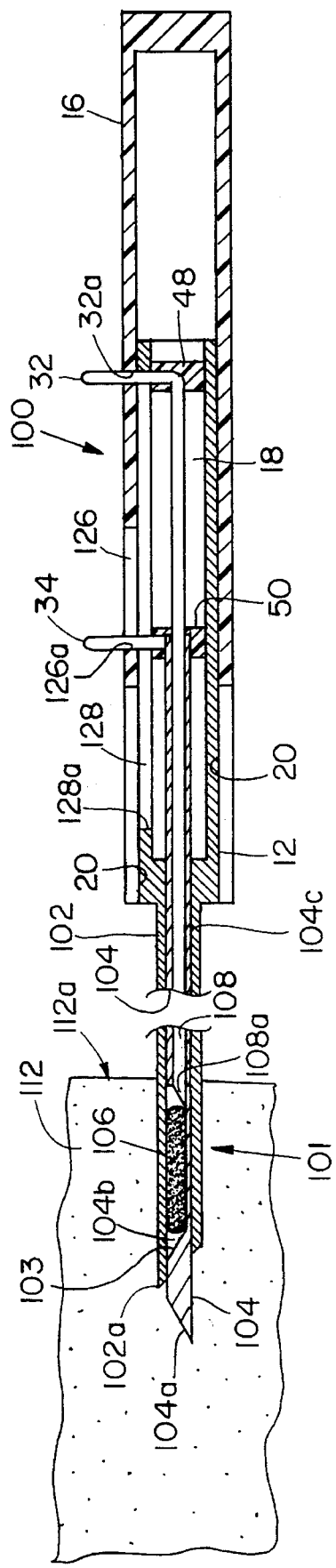
FIG. 6 is a cross-sectional side view of the instrument of FIG. 5 inserted into a portion of tissue in the fully retracted position.

Referring to FIGS. 5 and 6, instrument 100 is another preferred embodiment of the present invention. Instrument 100 differs from instrument 10 in that an outer tube 102 which is secured to housing 12 is mounted concentrically about cannula 104 and piston 108. Additionally, piston drive pin 32 and cannula drive pin 34 both extend through a single elongate slot 128 in housing 12. Housing slot 128 has a notch 128a located at its distal end for engaging cannula drive pin 34 when cannula drive pin 34 is in the advanced position. Piston drive pin 32 extends through driving member 16 through a hole 32a. Cannula drive pin 34 extends through driving member 16 through an elongate driving member slot 126. Driving member slot 126 has a notch 126a located at its distal end for engaging cannula drive pin 34.

Cannula 104 has a tip 104a which is angled for penetration into tissue. The tip 104a includes a cannula notch 104b for supporting a drug pellet 106. The cannula notch 104b has an inclined surface 103 located at its distal end. A bore 104c extending through cannula 104 between cannula notch 104b and the proximal end of cannula 104 allows piston 108 to slide within cannula 104. Piston 108 has a tip 108a which is angled at its distal end. Piston 108 is restricted from extending past cannula notch 104b by the inclined distal surface 103.

In operation, when depositing a drug pellet 106 into the tissue 112 of a patient, the surface 112a of tissue 112 is first cut with a scalpel. The tip 104a of cannula 104 is then inserted into the incision within tissue 112 while driving member 16 is in a retracted position and the distal end 101 of instrument 100 is advanced into tissue 112 until reaching a desired location. When driving member 16 is in a retracted position, cannula notch 104b is enclosed by outer tube 102 with tip 108a of piston 108 being at the proximal end of cannula notch 104b. Outer tube 102 protects drug pellet 106 and prevents it from tumbling out of cannula notch 104b prematurely. Alternatively, tip 104a of cannula 104 can be inserted into tissue 112 by puncturing the surface 112a of tissue 112 with tip 104a.

Driving member 16 is then moved distally along track 20 toward the distal end of piston 108 (FIG. 7). Cannula drive pin 34 is engaged within notch 126a of driving member slot 126 and piston drive pin 32 is engaged by hole 32a. As the driving member 16 is advanced, cannula 104 is extended from outer tube 102 such that cannula notch 104b and drug pellet 106 are exposed beyond the tip 102a of tube 102. At the same time, driving member 16 advances piston 108 by engaging piston drive pin 32 with hole 32a such that the cannula 104 and the piston 108 advance together in unison. Cannula 104 is extended until cannula drive pin 34 reaches the distal end of housing slot 128 where cannula drive pin 34 engages housing slot notch 128a.

As driving member 16 is further advanced, cannula drive pin 34 disengages from notch 126a in driving member slot 126 and piston drive pin 32 is advanced further, thereby advancing piston 108 forward relative to cannula 104 (FIG. 8). As piston 108 is extended into cannula notch 104b, drug pellet 106 is pushed against the inclined distal surface 103 of cannula notch 104b by piston 108. The angled tip 108a of piston 108 and the inclined distal surface 103 of cannula notch 104b displaces the drug pellet 106 laterally from cannula notch 104b into the surrounding tissue 112. Piston 108 is extended into cannula notch 104b until the proximal end of driving member slot 126 reaches cannula drive pin 34, thereby preventing further advancement of driving member 16. Further advancement of piston 108 is also prevented by the inclined distal surface 103 of cannula notch 104b.

Once the drug pellet 106 is deposited into tissue 112, the distal end 101 of instrument 100 can be removed from tissue 112. To remove distal end 101 from the tissue 112, the cannula 104 and the piston 108 are first retracted relative to outer tube 102 in the direction of arrows 124 and 122 (FIG. 9) by retracting driving member 16. This leaves behind the drug pellet 106 within tissue 112. Distal end 101 of instrument 100 is then pulled from tissue 112 in the direction of arrows 120 (FIG. 10) leaving behind a small puncture wound 106a.

The piston 108, cannula 104 and outer tube 102 are preferably formed of rigid sterilizable material such as stainless steel. Other components of the device, including the housing, driving member, piston and cannula grips, etc. are preferably made from low cost plastic material.

Equivalents

Those skilled in the art will know, or be able to ascertain using no more than routine experimentation, many equivalents to the specific embodiments of the invention described herein. For example, the term "drug" as used herein is intended to have a broad construction so as to include any type of medication capable of being administered subcutaneously in the manner described herein. Also, in the embodiment of FIGS. 1–4, the tip end of the piston longitudinally ahead of the drug may be provided with a post or barrier (not shown) of diameter slightly less than the diameter of the opening in the cannula 28 so that the drug is not only concentrically enclosed by the cannula until delivery but is also longitudinally enclosed by the barrier at the end of the piston. Furthermore, in the embodiment of FIGS. 5–10, the outer tube 102 can be omitted. In such a case, cannula notch 104b can have sidewalls to contain drug pellet 106. These and all other equivalents are intended to be encompassed by the following claims.

What is claimed is:

1. A subcutaneous drug delivery device comprising:
   a) a housing with a bore extending along a longitudinal axis of the housing and a track extending parallel to the bore, said track having an elongate housing slot extending along the longitudinal axis;
   b) a piston having a distal end;
   c) a cannula mounted concentric with the piston within the bore and extending along the longitudinal axis thereof with a distal end of the cannula extending beyond the distal end of the piston, the cannula having a cannula notch at the cannula distal end for supporting a drug, the cannula notch having a distal surface which extends distally outward and away from the housing to form an inclined surface upon which the drug can be pushed up for laterally ejecting the drug;
   d) a driving member slideably engaged in said track for longitudinal movement therein, the driving member having a hole formed therein;
   e) a piston drive pin for engaging the driving member hole for advancing the piston, the piston drive pin extending from the piston in a direction perpendicular to the longitudinal axis through the housing slot and the driving member hole;
   such that, as the driving member is moved distally along the track toward the piston distal end, the hole in the driving member is engaged by the piston drive pin and the piston is extended until the distal end of the piston reaches the distal surface of the cannula notch whereupon the piston distally pushes the drug up the inclined distal surface of the cannula notch to eject the drug laterally from the cannula notch.

2. The device of claim 1 further comprising an outer tube mounted concentric with the cannula and extending along the longitudinal axis, the outer tube being secured to the housing and being capable of enclosing the cannula notch.

3. The device of claim 2 further comprising:
   an elongate driving member slot extending along the longitudinal axis, the driving member slot having a notch formed therein; and
   a cannula drive pin for engaging the notch in the driving member slot for advancing the cannula, the cannula drive pin extending through the housing slot and the driving member slot, as the driving member is moved distally along the track toward the piston distal end, the notch in the driving member slot is engaged by the cannula drive pin and the cannula is extended until the cannula notch is extended beyond the outer tube.

4. The device of claim 3 further comprising a notch in the distal end of the housing slot for engaging the cannula drive pin.

5. The device of claim 1 wherein the piston has a proximal terminus which is mounted within a piston grip.

6. The device of claim 1 wherein the housing has finger grips extending therefrom transverse the longitudinal axis.

7. A subcutaneous drug delivery device comprising:
   a) a housing with a bore extending along a longitudinal axis of the housing and a track extending parallel to the bore, said track having an elongate housing slot extending along the longitudinal axis;
   b) a piston having a distal end;
   c) a cannula mounted concentric with the piston within the bore and extending along the longitudinal axis thereof with a distal end of the cannula extending beyond the distal end of the piston, the cannula having a cannula notch at the cannula distal end for supporting a drug, the cannula notch having a distal surface which extends distally outward and away from the housing to form an inclined surface upon which the drug can be pushed up for laterally ejecting the drug;
   d) a driving member slideably engaged in said track for longitudinal movement therein, the driving member having a hole formed therein;
   e) a piston drive pin for engaging the driving member hole for advancing the piston, the piston drive pin extending from the piston in a direction perpendicular to the longitudinal axis through the housing slot and the driving member hole;
   f) an outer tube mounted concentric with the cannula and extending along the longitudinal axis, the outer tube being secured to the housing and being capable of enclosing the cannula notch;
   g) an elongate driving member slot extending along the longitudinal axis, the driving member slot having a notch formed therein; and
   h) a cannula drive pin for engaging the notch in the driving member slot for advancing the cannula, the cannula drive pin extending through the housing slot and the driving member slot;
   such that, as the driving member is moved distally along the track toward the piston distal end, the notch in the driving member slot is engaged by the cannula drive pin and the hole in the driving member is engaged by the piston drive pin, the cannula and the piston being extended in unison until the cannula notch is extended beyond the outer tube, and as the driving member is extended further, the piston is extended until the distal end of the piston reaches the distal surface of the cannula notch whereupon the piston distally pushes the drug up the inclined distal surface of the cannula notch to eject the drug laterally from the cannula notch.

8. The device of claim 7 wherein the piston has a proximal terminus which is mounted within a piston grip.

9. The device of claim 7 further comprising a notch in the distal end of the housing slot for engaging the cannula drive pin.

10. The device of claim 7 wherein the housing has finger grips extending therefrom transverse the longitudinal axis.

11. A method for delivering a drug to a site within the body of an individual comprising:
   assembling a cannula concentrically about a piston along a longitudinal axis, the piston extending within a longitudinal bore of a housing for longitudinal movement along said bore, the cannula having a notch at a distal end of the cannula, the cannula notch having a distal surface;
   providing a drug within the cannula notch;
   mounting an outer tube concentrically about the cannula along the longitudinal axis, the outer tube being secured to the housing and being capable of enclosing the cannula notch;
   engaging a piston drive pin extending perpendicularly from the piston with a driving member having a hole formed therein, the driving member being mounted on a track in the housing for longitudinal movement, the track having an elongate housing slot;
   engaging a cannula drive pin extending perpendicularly from the cannula with the driving member, the cannula drive pin extending through the housing slot and through a driving member slot, the driving member slot having a notch formed therein;
   advancing the driving member along the track toward the piston distal end, such that the notch in the driving member slot is engaged by the cannula drive pin and the hole in the driving member is engaged by the piston drive pin, the cannula extending until the cannula notch is extended beyond the outer tube, the piston extending until the distal end of the piston reaches the distal surface of the cannula notch whereupon the piston pushes the drug against the distal surface of the cannula notch to eject the drug laterally from the cannula notch.

12. The method of claim 11 further comprising the step of engaging the cannula drive pin with a notch in the distal end of the housing slot.

13. A method for delivering a drug to a site within the body of an individual comprising:
   a) assembling a cannula concentrically about a piston along a longitudinal axis, the piston extending within a longitudinal bore of a housing for longitudinal movement along said bore, the cannula having a notch at a distal end of the cannula, the cannula notch having a distal surface;
   b) providing a drug within the cannula notch;
   c) mounting an outer tube concentrically about the cannula along the longitudinal axis, the outer tube being secured to the housing and being capable of enclosing the cannula notch;
   d) engaging a piston drive pin extending perpendicularly from the piston with a driving member having a hole formed therein, the driving member being mounted on a track in the housing for longitudinal movement, the track having an elongate housing slot;
   e) engaging a cannula drive pin extending perpendicularly from the cannula with the driving member, the cannula drive pin extending through the housing slot and through a driving member slot, the driving member slot having a notch formed therein;
   f) advancing the driving member along the track toward the piston distal end, such that the notch in the driving member is engaged by the cannula drive pin and the hole in the driving member is engaged by the piston drive pin, the cannula and the piston being extended in unison until the cannula notch is extended beyond the outer tube, and as the driving member is extended further, the piston is extended until the distal end of the piston reaches the distal surface of the cannula notch whereupon the piston pushes the drug against the distal surface of the cannula notch to eject the drug laterally from the cannula notch.

14. The method of claim 13 further comprising the step of engaging the cannula drive pin with a notch in the distal end of the housing slot.

15. A method for delivering a drug to a site within the body of an individual comprising:

a) assembling a cannula concentrically about a piston along a longitudinal axis, the piston extending within a longitudinal bore of a housing for longitudinal movement along said bore, the cannula having a notch at a distal end of the cannula, the cannula notch having a distal surface which extends distally outward and away from the housing to form an inclined surface upon which drugs can be pushed up and laterally ejected;

b) providing a drug within the cannula notch;

c) engaging a piston drive pin extending perpendicularly from the piston with a driving member having a hole formed therein, the driving member being mounted on a track in the housing for longitudinal movement, the track having an elongate housing slot;

d) advancing the driving member along the track toward the piston distal end, the hole in the driving member engaging the piston drive pin, the piston extending until the distal end of the piston reaches the distal surface of the cannula notch whereupon the piston distally pushes the drug up the inclined distal surface of the cannula notch to eject the drug laterally from the cannula notch.

16. A biological agent delivery device comprising:

a cannula having a distal end and a proximal end, the cannula having a longitudinally extending wall with a notch formed in said wall near the distal end for containing a biological agent, the cannula notch having a distal surface which extends distally outward and away from the proximal end of the cannula to form an inclined surface; and a displacement member disposed within the wall of the cannula for movement relative to the cannula to push the biological agent up the inclined distal surface of the cannula notch to deliver the biological agent laterally from the cannula notch.

17. The delivery device of claim 16 in which the displacement member comprises a piston.

18. The delivery device of claim 17 in which the piston has a angled tip.

19. The delivery device of claim 16 further comprising an outer tube mounted concentric with the cannula and extending along a portion of the cannula, the outer tube being slidable relative to the cannula and capable of enclosing the cannula notch.

20. A product delivery device comprising:

a cannula having a distal end and a proximal end, the cannula having a longitudinally extending wall with a notch formed in said wall near the distal end for containing a product, the cannula notch having a distal surface which extends distally outward and away from the proximal end of the cannula to form an inclined surface; and a displacement member disposed within the wall of the cannula for movement relative to the cannula to push the product up the inclined distal surface of the cannula notch to deliver the product laterally from the cannula notch.

21. The delivery device of claim 20 in which the displacement member comprises a piston.

22. The delivery device of claim 20 further comprising an outer tube mounted concentric with the cannula and extending along a portion of the cannula, the outer tube being slidable relative to the cannula and capable of enclosing the cannula notch.

* * * * *